United States Patent [19]

Hulme et al.

[11] Patent Number: 4,778,946
[45] Date of Patent: Oct. 18, 1988

[54] PROCESS FOR SEPARATING ETHYLBENZENE FROM FEEDSTREAM CONTAINING METAXYLENE USING A ZEOLITE ADSORBENT

[75] Inventors: Roger Hulme, Linden; Denise M. Barthomeuf, Cranford, both of N.J.

[73] Assignee: Exxon Research and Engineering Company, Florham Park, N.J.

[21] Appl. No.: 52,178

[22] Filed: May 4, 1987

Related U.S. Application Data

[63] Continuation of Ser. No. 604,481, Apr. 27, 1984, abandoned, which is a continuation of Ser. No. 426,242, Sep. 28, 1982, abandoned.

[51] Int. Cl.$^4$ .............................................. B01D 53/04
[52] U.S. Cl. .................................. 585/828; 208/310 Z
[58] Field of Search ........................ 208/310 Z; 585/828

[56] References Cited

U.S. PATENT DOCUMENTS

| | | | |
|---|---|---|---|
| 3,130,007 | 4/1954 | Breck | 208/DIG. 2 |
| 3,558,730 | 1/1971 | Neuzil | 585/828 |
| 3,626,020 | 12/1971 | Neuzil | 208/310 Z |
| 3,665,046 | 5/1972 | De Rosset | 208/310 Z |
| 3,686,342 | 8/1972 | Neuzil | 585/828 |
| 3,686,343 | 8/1972 | Bearden, Jr. et al. | 208/310 Z |
| 3,734,974 | 5/1973 | Neuzil | 585/831 |
| 3,795,711 | 3/1974 | Worrell et al. | 585/828 |
| 3,855,333 | 12/1974 | Neuzil | 585/828 X |
| 3,917,734 | 11/1975 | de Rosset | 585/828 |
| 3,943,182 | 3/1982 | Neuzil et al. | 585/828 |
| 4,021,499 | 5/1977 | Bieser | 585/828 |
| 4,028,428 | 6/1977 | Neuzil et al. | 585/828 |
| 4,108,915 | 8/1978 | Rosback et al. | 585/828 |
| 4,283,587 | 8/1981 | Rosback et al. | 585/828 |
| 4,326,092 | 4/1982 | Neuzil | 585/828 |
| 4,393,266 | 7/1983 | Smolin | 585/828 |

FOREIGN PATENT DOCUMENTS 1354716  5/1974  United Kingdom ............... 585/828

*Primary Examiner*—Glenn Caldarola
*Attorney, Agent, or Firm*—Richard E. Nanfeldt

[57] ABSTRACT

Ethylbenzene is separated from a paraxylene depleted feedstream containing meta-xylene by contacting the feedstream with a K-substituted Type Y zeolite, passing through the zeolite a selected desorbent, and recovering a stream enhanced in concentration of ethylbenzene relative to meta-xylene. Preferably, the desorbent is an aromatic hydrocarbon.

The zeolite may contain an effective amount up to 10% by weight of total water and up to about 4% by weight methanol.

8 Claims, No Drawings

PROCESS FOR SEPARATING ETHYLBENZENE FROM FEEDSTREAM CONTAINING METAXYLENE USING A ZEOLITE ADSORBENT

This application is a continuation of application Ser. No. 604,481 filed 4/27/84, abandoned, which is a continuation of application Ser. No. 426,242, filed 9/28/82, abandoned.

BACKGROUND OF THE INVENTION

1. Field of the Invention

This invention relates to a process for separating ethylbenzene from a feedstream containing meta-xylene wherein a zeolite is employed as selective adsorbent.

2. Description of Related Disclosures

A class of crystalline aluminosilicates, commonly known as zeolites, constitutes well known adsorbents for use in separating certain hydrocarbon compounds from mixtures thereof. In particular, zeolites are widely used for selective separation of para-xylene from mixtures thereof with other $C_8$ aromatic compounds such as meta- and/or ortho-xylene and/or ethylbenzene. For example, U.S. Pat. Nos. 3,636,121; 3,686,342; 3,686,343; 3,835,043; 3,855,333; 3,878,127; 3,894,108; 3,903,187 and 4,265,788 are all directed toward methods of separating para-xylene from mixtures thereof with various hydrocarbons or of selectively obtaining para-xylene and ethylbenzene from a mixture containing other components, using various types of zeolites as adsorbent. In U.S. Pat. No. 3,668,267 selective separation of 2,7-dimethylnaphthalene from a dimethylnaphthalene concentrate is effected using sodium Type Y zeolite.

While separation and recovery of para-xylene from other xylene isomers or ethyl benzene is desirable since para-xylene is an important raw material for the synthesis of terephthalic acid, it has become increasingly desirable to recover ethylbenzene selectively from feedstreams containing ethylbenzene and other xylene isomers. This is because of its commercial importance in the manufacture of styrene monomer and its increasing cost of production from reaction of benzene with ethylene. Feedstreams containing ethylbenzene and metaxylene may be obtained as by-products from a separation of para-xylene therefrom or may be produced by a solvent extraction or fractionation process from a pyrolysis gasoline or from a naphtha reformed with a catalyst which is an oxide containing platinum and halogen.

It is know that potassium—substituted Type Y zeolites having the faujasite structure selectively adsorb ethylbenzene from mixtures comprising ethylbenzene, meta-xylene and ortho-xylene using toluene as a desorbent. U.S. Pat. No. 3,998,901 teaches that ethylbenzene can be separated from xylene isomers using a Type Z zeolite substituted with Sr and K wherein ethane or lower gases or toluene is used as desorbant. According to U.S. Pat. No. 3,943,182, desorbents other than toluene such as diethylbenzene and/or benzene selectively separate ethylbenzene from a mixture containing ethylbenzene and at least one xylene isomer using a Type X zeolite. It is also disclosed that selectivity for ethylbenzene over its isomers decreases as the silica to alumina ratio in the zeolite is increased above 3.0 (i.e., using a Type Y zeolite).

U.S. Pat. No. 3,943,182 further teaches that the presence of water in the zeolite in amounts of 0.02 to 2.5% by weight measured by loss on ignition at 500° C. optimizes selectivity for ethylbenzene. Other patents disclose that certain compounds will modify the adsorbent characteristics of zeolites when contacted therewith. For example, in the context of aromatic isomer separation, U.S. Pat. No. 3,698,157 discloses that an organic radical-substituted silane modifies the characteristics of a selected zeolite in the separation of $C_8$ aromatic isomers. In U.S. Pat. No. 3,734,974 it is taught that faster exchange rates and reduced ortho- and meta-xylene tailing are accomplished by adding small amounts of water to a particular adsorbent. Moreover, U.S. Pat. No. 3,855,333 is directed to use, as an adsorbent, of a zeolite containing 0.1 to 8.0% by weight of an alcohol to obtain increased selectivity of the zeolite for adsorption of para-xylene.

SUMMARY OF THE INVENTION

The invention disclosed herein is directed to the discovery that the selectivity factor of a zeolite adsorbent for ethylbenzene over meta-xylene as defined below is not a constant number and may be substantially improved, by the judicious choice of a third component as the desorbent, over that obtained using conventionally employed desorbents, such as toluene. In addition, it is found that the optional use of water and/or an additive compound such as an alcohol, ammonia or pyrrole up to a maximum total content in the zeolite may optimize the strength of the desorbent without adversely affecting the selectivity factor for purposes of maximizing recovery of ethylbenzene.

It has now been found that ethylbenzene can be separated and recovered from a feedstream mixture containing meta-xylene and substantially depleted in para-xylene by a process comprising (a) contacting the mixture with a potassium—substituted Type Y zeolite which optionally contains during the contacting step (1) an effective amount up to 10% by weight of total water or (2) an effective amount up to 10% by weight of both total water and an additive compound other than water, which additive compound contains at least one Group VA, VIA, or VIIA atom, wherein the contacting takes place under conditions so as to effect the selective adsorption of the ethylbenzene by the zeolite, (b) passing through the zeolite, during or after the contacting step, a desorbent (other than toluene) which produces a selectivity factor ($\alpha_{EB/meta}$) for the zeolite which is greater than that produced when toluene is employed as a desorbent (and preferably greater than that produced in the absence of desorbents) under the same conditions, and which has a desorbent strength factor ($\alpha_{EB/desorbant}$) in the range of from 0.1 to 10, measured as described below, and (c) recovering from the zeolite a stream enhanced in concentration of ethylbenzene relative to meta-xylene.

The selectivity factor, which represents the selectivity of the adsorbent for ethylbenzene over meta-xylene, is defined by the expression:

$$\alpha_{EB/meta} = \frac{\text{Amount of ethylbenzene in zeolite}}{\text{Amount of ethylbenzene in free liquid}} \times \frac{\text{Amount of meta-xylene in free liquid}}{\text{Amount of meta-xylene in zeolite}}$$

The desorbent strength factor, which represents the selectivity of the adsorbent for ethylbenzene over the desorbent, is defined by the expression:

$$\alpha_{EB/desorbent} = \frac{\text{Amount of ethylbenzene in zeolite}}{\text{Amount of ethylene in free liquid}} \times$$

$$\frac{\text{Amount of desorbent in free liquid}}{\text{Amount of desorbent in zeolite}}$$

DESCRIPTION OF THE PREFERRED EMBODIMENTS

The feedstream mixtures which are applicable to the present invention comprise at least ethylbenzene and meta-xylene and are substantially depleted in para-xylene, i.e., contain no more than about 5% by weight of para-xylene. Other components which may be present in the mixture include ortho-xylene isomers or other aromatic hydrocarbons such as alkyl-substituted benzenes. In addition, the feedstream mixture may contain up to about 20 volume percent, preferably less than about 10 volume percent, of nonaromatic components such as paraffins or cycloaliphatic or olefinic compounds. Such components will tend to be least adsorbed by the zeolite. It is noted, however, that whatever other components may be contained in the mixture, the process herein embodies a technique for separating ethylbenzene from meta-xylene.

A feedstream mixture containing several $C_8$ aromatic isomers such as ethylbenzene and the xylene isomers is generally obtained, e.g., through reforming, pyrolysis or isomerization processes. Substantially all the para-xylene isomer is then separated from this mixture such as by crystallization, extraction, or selective adsorption of para-xylene, thus leaving a feedstream relatively rich in ethylbenzene and meta-xylene and substantially depleted in para-xylene which is suitable for the separation process of the present invention.

In the process herein, the ethylbenzene is separated the meta-xylene in the feedstream mixture by contacting the mixture with the zeolite adsorbent defined below such that the ethylbenzene is more selectively adsorbed than the meta-xylene. Concurrently with this contacting step, or subsequent thereto (if the operation is a batch operation), a desorbant is passed through the zeolite so as to desorb the adsorbed phase which has been enriched in ethylbenzene.

It will be recognized that contacting of the zeolite with the feedstream mixture and the desorbent may be conducted in a batch or continuous mode of operation. For example, the adsorbent may be employed as a dense compact fixed bed which is alternately contacted with the feedstream mixture and desorbent or may be a fluidized bed contacted with the mixture and desorbent in a continuous operation with or without magnetic stabilization and with or without real or simulated co- or countercurrent flows. Where the adsorbent is employed as a single static bed it may be semi-continuous, i.e., operated as a pulsed chromatographic process; or a set of two or more static beds may be employed such that the feedstream mixture is contacted with one bed while the desorbent is passed through the other. It may be desired to remove the least-adsorbed components from the voids in the bed by flushing with a very weakly adsorbed material, e.g., a paraffin, before recovery of the ethylbenzene by addition of desorbent. Moving or simulated moving beds represent, however, a preferred mode of operation because of the greater efficiency in separation obtained.

Temperatures for the contacting and desorption steps of the process herein may vary broadly depending, for example, on the desorbent used, but generally will range from about room temperature to about 300° C. Similarly, operating pressures will vary considerably, usually from atmospheric to about 30 atm (3 mega-pascals) in pressure.

The desorbent employed in the present invention may be defined herein as a compound which is characterized by its minimum ability to enhance the selectivity of the adsorbent zeolite for separating the ethylbenzene from meta-xylene and by its optimal strength as a desorbent. The selectivity is expressed herein as a selectivity factor, designated $\alpha_{EB/meta}$, which is defined above; its relevance to a batch operation will be recognized readily by the practitioner. In a chromatographic separation, $\alpha_{EB/meta}$ is, to a large extent, a measure of the degree of separation between the peaks issuing from the column. The value of the selectivity factor should be as high as possible; if it is too low the ethylbenzene and meta-xylene peaks will overlap, resulting in poor separation of the two components. For purposes of this invention the selectivity factor of the zeolite is greater than that produced in the presence of toluene (i.e., if toluene is used as the desorbent), and preferably greater than that produced in the absence of desorbents, under the same conditions. For example, as a guideline, $\alpha_{EB/meta}$ should be at least about 2.0, and preferably at least about 3.2, when measured under ambient conditions of temperature and pressure using about 300 mg of zeolite contacted with a feed, in an amount of about 22% of the zeolite weight, composed of two-thirds by weight of desorbent and one-third by weight of the mixture containing ethylbenzene and meta-xylene.

The other parameter which characterizes the desorbent herein is the strength of the desorbent, which is expressed herein by a desorbent strength factor, designated $\alpha_{EB/desorbent}$ and defined above. This factor represents the ratio of the adsorption strength of the zeolite for the ethylbenzene to the adsorption strength of the zeolite for the desorbent. If the desorbent is too strong relative to ethylbenzene so that $\alpha_{EB/desorbent}$ is less than 0.1, e.g., when water or ammonia is used as the desorbent, both ethylbenzene and meta-xylene will be eluted in overlapping peaks. On the other hand, a weak desorbent, with $\alpha_{EB/desorbent}$ greater than 10, will not compete favorably with the ethylbenzene, necessitating large volumes of desorbent to recover all the ethylbenzene. The ethylbenzene thus collected would be contained in large amounts of the desorbent so that expensive distillation procedures would be required to recover the ethylbenzene therefrom. The ratio is preferably in the region of 1–2, but for purposes herein $\alpha_{EB/desorbent}$ is generally in the range of from about 0.1 to 10, and preferably about 0.5 to 4.0 when measured under ambient conditions of temperature and pressure using about 300 mg of zeolite contacted with a feed, in an amount of about 22% of the zeolite weight, composed of two-thirds by weight of the desorbent and one-third by weight of a mixture containing ethylbenzene and meta-xylene.

It can be seen that both the selectivity as measured by $\alpha_{EB/meta}$ produced by the desorbent and the desorbent strength as measured by $\alpha_{EB/desorbent}$ are important in obtaining reasonable separation of ethylbenzene from meta-xylene and that those desorbents which fall in the preferred ranges for both factors will be most desirable.

The desorbents which may be applicable herein include such compounds as alcohols, ethers, esters, halogenated hydrocarbons, aromatic hydrocarbons or any other compounds which will meet the selectivity and desorbent strength requirements specified above. Preferably, the desorbent is one or more aromatic hydrocarbons, more preferably benzene, indane, or alkyl-substituted benzenes, provided, of course, that they meet the above-mentioned criteria for selectivity and desorbent strength. Thus, for example, toluene is not a suitable desorbent herein. Representative compounds which fall within this category include tetralin, isobutylbenzene, 1-methyl-2-n-propylbenzene, 1-methyl-3-n-propylbenzene, 1,2,4-trimethylbenzene(pseudocumene), 1,2,3-trimethylbenzene and 1,3,5-trimethylbenzene(mesitylene), indane, benzene, orthoxylene, 1,2,3,4-tetramethylbenzene(prehnitene), 1,2,4,5-tetramethylbenzene, and 1,2,3,5-tetramethylbenzene, meta-diethylbenzene, 1,3-diisopropylbenzene, ortho-diethylbenzene, pentamethylbenzene, and the like. Among these, the preferred desorbents herein are otho-diethylbenzene, mesitylene, benzene, prehnitene, pseudocumene, and pentamethylbezene, most preferably, ortho-diethylbenzene, prehnitene, mesitylene and benzene. In addition, mixtures of two or more desorbents which have the requisite characteristics may also be employed as desorbent if desired. Additionally, the desorbent may be diluted with a liquid inert material such as a paraffin or cycloparaffin.

The zeolite adsorbent to be employed in the process of this invention is a synthetic crystalline aluminosilicate of Type Y (having the faujasite structure) containing potassium rather than sodium as the cation. The Type Y zeolites are described in U.S. Pat. No. 3,130,007, the disclosure of which is incorporated herein by reference. For purposes of the present invention a useful representative hydrated zeolite used as starting material is of the formula, which is not intended to be limiting in any respect:

$$(0.9 \pm 0.2)K_2O:Al_2O_3:wSiO_2:xH_2O$$

wherein w is a value greater than about 3 and x is any value up to about 9.

Zeolites from which substantially all the water has been removed before use as adsorbent by, e.g., heating, evacuation, displacement by hydrocarbons, etc., or by combinations thereof, are found to be particularly suited to the present invention. Such dried zeolites may contain from 1 to 2% by weight of water, depending on the drying temperature, measured by loss on ignition at 1000° C. It has been found that if water is added to this dried zeolite (to yield an effective amount up to 10% by weight of total water content in the zeolite, measured by loss on ignition at 1000° C.), the desorbent strength may be improved without greatly sacrificing selectivity for ethylbenzene over meta-xylene. The addition of water is found to be particularly effective for improving the desorbent strength (i.e., bringing the $\alpha_{EB/desorbent}$ closer to the regio of 1-2), of, for example, ortho-diethylbenzene, mesitylene, benzene and prehnitene under the conditions described in the examples hereinbelow.

As an alternative, the zeolite, which is preferably previously dried as described above, may contain an effective total amount up to 10% by weight (measured, e.g., by loss on ignition at 1000° C.) of both total water and an additive compound other than water containing at least one atom selected from the Group VA, VIA, and VIIA elements, i.e., a heteroatom such as nitrogen, phosphorus, oxygen, sulfur, fluorine or chlorine. Preferably, the heteroatom is selected from the Group VA and VIA elements, more preferably, oxygen and nitrogen. Examples of these preferred additives include alcohols, ammonia and pyrrole. Particularly preferred additives herein are methonal and ammonia. Mixtures of these additive compounds may also be employed. The addition of such compounds to the zeolite may have the effect observed herein on addition of water to the zeolite in that the desorbent strength factor is brought to an optimum level nearest to unity. This effect is observed, for example, when o-diethylbenzene, mesitylene, prehnitene or benzene is used as desorbent for a zeolite containing either ammonia or methanol under the conditions described in the examples below.

The optimum effective amounts of water and/or other additive compound in the zeolite will depend mainly on the desorbent being employed. With some desorbents, for example, the desorbent strength factor will be improved without adversely affecting the selectivity factor or even improving the selectivity as the content of water or other additive compound is increased in the zeolite. With other desorbents, while the desorbent strength is improved, the selectivity factor is decreased to varying extents, although usually not significantly, so that there is a balance as to the amount of water or additive compound to be employed. With still other desorbents, increasing the amount of water or additive compound will not improve or will adversely affect the desorbent strength while possibly decreasing or increasing the selectivity factor. By performing the relatively simple tests described in Examples II and III below, however, the practitioner will readily be able to determine which desorbents will benefit from addition of the water and/or additive compound, and the practitioner can select the appropriate desorbent and effective amount of additive compound and water to achieve the best balance of factors for separation of the ethylbenzene. Notwithstanding the amount of water or additive compound used, the selectivity factor and desorbent strength factor should in any event be within the required ranges specified above to be useful in the separation process herein. As a guideline, however, depending on the desorbent, the preferred total water content in the zeolite is up to 5% by weight and the preferred total content of additive compound present in the zeolite is up to 4% by weight of the zeolite. It is to be further noted that when additive compounds (other than water) are present in the zeolite the total amount of water present is preferably no greater than about 4% by weight, and more preferably is 1.5 to 2%.

After the feedstream mixture and desorbent have been contacted with the zeolite, the respective eluted product streams containing the various components are directed to separate collection veseels. The stream recovered, which is enhanced in the amount of ethylbenzene relative to the meta-xylene in the mixture (due to the separation achieved by the adsorption and desorption operations), may be processed so as to recover the ethylbenzene as by, e.g., distillation from the desorbent or by other suitable recovery techniques.

The following examples further illustrate the efficacy of the present invention. In these examples all parts and percentages are given by weight and all temperatures are in degrees Celsius unless otherwise indicated.

EXAMPLE I

A series of 34 feeds were prepared containing 17% by weight ethylbenzene, 17% by weight meta-xylene and 66% by weight of the hydrocarbon desorbent indicated in Table I (with sample 20 containing no desorbent).

Potassium Type Y faujasite was dried at 550° C. in a stream of dry nitrogen (containing less than 5 ppm H₂O), so that the faujasite lost 1.5% of its weight on ignition at 1000° C. Approximately 300 mg samples of the zeolite were transferred to a series of 2-ml vials sealed with a septum cap. To each bottle was added, by syringe, the respective feed in an amount of 22% of the weight of the zeolite, representing the capacity of the zeolite. The vials were agitated at room temperature for 24 hours under ambient conditions followed by addition of 1 ml of isooctane to facilitate analysis of the traces of hydrocarbons unadsorbed by the zeolite in equilibrium with the adsorbed phase. After further agitation the isooctane was removed and analyzed by gas chromoatography for ethylbenzene, meta-xylene and desorbent. From the peaks in the gas chromatograms the $\alpha_{EB/meta}$ and $\alpha_{EB/desorbent}$ factors are defined hereinabove were determined and are indicated in Table I.

TABLE I

| Sample | Desorbent | $\alpha EB/meta$ | $\alpha EB/$ desorbent |
|---|---|---|---|
| 1 | toluene* | 1.9 | 1.9 |
| 2 | para-ethyltoluene | 1.9 | 0.25 |
| 3 | t-butylbenzene | 2.0 | 2.3 |
| 4 | 1,4-diisopropylbenzene | 2.0 | 0.22 |
| 5 | isopropylbenzene | 2.1 | 0.73 |
| 6 | isobutylbenzene | 2.1 | 3.7 |
| 7 | 1-methyl-2-isopropylbenzene | 2.3 | 0.6 |
| 8 | 1-methyl-4-n-propylbenzene | 2.3 | 0.6 |
| 9 | para-diethylbenzene | 2.3 | 0.19 |
| 10 | para-xylene | 2.5 | 0.6 |
| 11 | n-propylbenzene | 2.5 | 1.75 |
| 12 | 1-methyl-3-isopropylbenzene | 2.5 | 0.8 |
| 13 | 1-methyl-2-ethylbenzene | 2.7 | 0.95 |
| 14 | sec-butylbenzene | 2.7 | 2.4 |
| 15 | 1-methyl-4-isopropylbenzene | 2.7 | 0.06 |
| 16 | 1,3-diisopropylbenzene | 2.7 | 0.96 |
| 17 | n-butylbenzene | 2.8 | 4.25 |
| 18 | tetralin | 2.9 | 0.45 |
| 19 | 1-methyl-3-ethylbenzene | 3.0 | 1.65 |
| 20 | None* | 3.2 | — |
| 21 | 1-methyl-2-n-propylbenzene | 3.2 | 1.0 |
| 22 | pseudocumene | 3.3 | 1.4 |
| 23 | indane | 3.4 | 1.8 |
| 24 | meta-diethylbenzene | 3.5 | 0.5 |
| 25 | 1-methyl-3-n-propylbenzene | 3.5 | 2.3 |
| 26 | benzene | 4.1 | 7.3 |
| 27 | ortho-xylene | 4.3 | 4.6 |
| 28 | pentamethylbenzene | 4.7 | 3.0 |

TABLE I-continued

| Sample | Desorbent | $\alpha EB/meta$ | $\alpha EB/$ desorbent |
|---|---|---|---|
| 29 | 1,2,4,5-tetramethylbenzene | 5.3 | 5.1 |
| 30 | mesitylene | 5.5 | 7.0 |
| 31 | 1,2,3,5-tetramethylbenzene | 5.8 | 3.8 |
| 32 | 1,2,3-trimethylbenzene | 6.1 | 4.75 |
| 33 | ortho-diethylbenzene | 6.4 | 2.2 |
| 34 | prehnitene | 6.8 | 1.9 |

*Comparative examples

Each desorbent tested was found to effect better separation of ethylbenzene from meta-xylene than toluene. It can be seen from the results that toluene, a conventionally used desorbent, produces one of the lowest selectivity factors ($\alpha_{EB/meta}$).

EXAMPLE II

This example illustrates the effect of adding water to the zeolite on its selectivity for ethylbenzene and on the strength of several desorbents.

The procedure of Example I was followed using the desorbents listed in Table II and adding to the zeolite (which after drying contained 1.5% water as determined by loss on ignition at 1000° C.), before contacting it with the feed, an amount of water which resulted in a total water content, as determined by loss on ignition at 1000° C., indicated in Table II. The $\alpha_{EB/meta}$ and $\alpha_{EB/desorbent}$ factors are indicated in the table.

TABLE II

| Desorbent | Water Content (%) | $\alpha EB/meta$ | $\alpha EB/$ desorbent | Change (%) in Desorbent Strength on Addition of Water (Relative to Strength for 1.5% Water Content) |
|---|---|---|---|---|
| ortho-diethylbenzene | 1.5 | 6.4 | 2.2 | — |
|  | 4.4 | 5.4 | 1.0 | +55 |
| mesitylene | 1.5 | 5.5 | 7.0 | — |
|  | 4.7 | 4.8 | 4.2 | −40 |
| benzene | 1.5 | 4.1 | 7.3 | — |
|  | 4.9 | 3.9 | 5.2 | +30 |
|  | 6.5 | 2.8 | 2.3 | +68 |
| prehnitene | 1.5 | 6.8 | 1.9 | — |
|  | 4.5 | 7.5 | 1.1 | +41 |
| pseudocumene | 1.5 | 3.3 | 1.4 | — |
|  | 4.5 | 3.1 | 1.3 | +10 |
| toluene* | 1.5 | 1.9 | 1.9 | — |
|  | 4.5 | 3.5 | 2.0 | −5 |
| meta-ethyltoluene | 1.5 | 3.0 | 1.6 | — |
|  | 5.0 | 3.6 | 1.9 | −20 |

*Comparative example

It can be seen from the data that the addition of water can diametrically affect the effective strength of the desorbent. In all cases where the presence of water increases the strength of the desorbent, the selectivity of the zeolite for ethylbenzene over meta-xylene remains acceptably high.

EXAMPLE III

This example illustrates the effect of adding ammonia or methanol to the zeolite on its selectivity for ethylbenzene over meta-xylene and on the strength of the desorbent.

The procedure of Example I was followed using the desorbents listed in Table III and adding to the zeolite (which after drying contained 1.5% water as determined by loss on ignition at 1000° C.), before contacting it with the feed, an amount of ammonia or methanol to give the contents of each shown in Table III. The $\alpha_{EB/}$ meta and $\alpha_{EB/desorbent}$ selectivity factors are indicated in the table.

TABLE III

| Desorbent | NH$_3$ Content (%) | CH$_3$OH Content (%) | αEB/meta | αEB/desorbent | Change (%) in Desorbent Strength on Addition of NH$_3$ or CH$_3$OH (Relative to Strength for 1.5% Water Content) |
|---|---|---|---|---|---|
| o-diethylbenzene | 0 | 0 | 6.4 | 2.2 | — |
| | 4 | 0 | 4.2 | 0.9 | +60 |
| | 0 | 3.4 | 5.7 | 1.1 | +50 |
| mesitylene | 0 | 0 | 5.5 | 7.0 | — |
| | 4 | 0 | 4.3 | 4.0 | +43 |
| | 0 | 3.6 | 4.9 | 5.8 | +17 |
| benzene | 0 | 0 | 4.1 | 7.3 | — |
| | 1.4 | 0 | 4.0 | 6.6 | +8 |
| | 5.2 | 0 | 3.0 | 1.9 | +74 |
| | 0 | 3.2 | 4.1 | 5.0 | +32 |
| | 0 | 5.2 | 4.3 | 4.0 | +45 |
| prehnitene | 0 | 0 | 6.8 | 1.9 | — |
| | 4 | 0 | 3.5 | 1.1 | +42 |
| | 0 | 3.4 | 7.7 | 1.8 | +5 |
| pseudocumene | 0 | 0 | 3.3 | 1.4 | — |
| | 4 | 0 | 3.0 | 1.2 | −15 |
| | 0 | 3.2 | 3.6 | 1.5 | −7 |
| m-ethyltoluene | 0 | 0 | 3.0 | 1.6 | — |
| | 4 | 0 | 3.9 | 1.7 | −5 |
| | 0 | 3.4 | 3.2 | 1.6 | 0 |

It is noted that marked improvements in desorbent strength are achieved for many desorbents tested without significantly sacrificing the selectivity factor.

In summary, the present invention is seen to provide an improved process for separating ethylbenzene from meta-xylene wherein a potassium Type Y zeolite is employed as the selective adsorbent and wherein a selected compound is employed as the desorbent.

What is claimed is:

1. A process for separating ethylbenzene from a feedstrom containing metaxylene but substantially depleted in paraxylene which comprises the steps of:
    (a) contacting with feedstream with a potassium-substituted Type Y zeolite which contains up to 10% by weight of total water and an amount up to about 4% of an additive compound, which additive compound is methanol, under conditions for the adsorption of ethylbenzene by the zeolite;
    (b) passing through the zeolite, during or after the contacting step, a desorbent which produces a selectivity of factor for the zeolite which is greater than that produced when toluene is employed as a desorbent under the same conditions and which has a desorbent strength factor in the range from 0.1 to 10; and
    (c) recovering from said zeolite a stream enhanced in ethylbenzene concentration relative to metaxylene.

2. The process of claim 1 wherein said zeolite contains up to 5% by weight of total water.

3. The process of claim 1 wherein said desorbent produces a selectivity factor of at least 2 and has a desorbent strength factor of between 0.5 and 4.

4. The process of claim 1 wherein said desorbent is an aromatic hydrocarbon.

5. The process of claim 4 wherein said desorbent is o-diethylbenzene, mesitylene, benzene, prehnitene, pseudocumene, or pentamethylbenzene.

6. The process of claim 1 wherein said desorbent is ortho-diethylbenzene, mesitylene, benzene or prehnitene.

7. The process of claim 1 wherein the separation is conducted in a batch operation.

8. The process of claim 1 wherein the separation is conducted in a continuous operation.

* * * * *